(12) United States Patent
Coel et al.

(10) Patent No.: US 9,907,305 B2
(45) Date of Patent: Mar. 6, 2018

(54) PRODUCTION OF DISINFECTING SOLUTIONS

(71) Applicant: SOLVAY SA, Brussels (BE)

(72) Inventors: Philippe Coel, Brussels (BE); Pierre Dournel, Brussels (BE); Pierre Miquel, Roubaix (FR)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 15/455,504

(22) Filed: Mar. 10, 2017

(65) Prior Publication Data

US 2017/0273302 A1     Sep. 28, 2017

Related U.S. Application Data

(60) Provisional application No. 62/311,475, filed on Mar. 22, 2016.

(51) Int. Cl.
*A01N 37/02* (2006.01)
*A01N 37/36* (2006.01)
*A01N 59/00* (2006.01)

(52) U.S. Cl.
CPC ............ *A01N 37/36* (2013.01); *A01N 37/02* (2013.01); *A01N 59/00* (2013.01)

(58) Field of Classification Search
CPC ....... C07C 407/00; A01N 37/36; A01N 37/02; A01N 59/00
See application file for complete search history.

(56) References Cited

U.S. PATENT DOCUMENTS

| | | | |
|---|---|---|---|
| 3,329,610 A | 7/1967 | Kreuz et al. | |
| 3,360,531 A | 12/1967 | French et al. | |
| 3,432,546 A | 3/1969 | Oringer et al. | |
| 5,349,083 A | 9/1994 | Brougham et al. | |
| 5,368,867 A | 11/1994 | Da Silva et al. | |
| 5,977,403 A | 11/1999 | Byers | |
| 7,547,421 B2 * | 6/2009 | McSherry | C07C 407/00 422/105 |
| 7,737,298 B2 | 6/2010 | Kline et al. | |
| 8,828,910 B2 | 9/2014 | Aksela et al. | |
| 8,975,450 B2 | 3/2015 | Scates | |
| 2015/0291520 A1 | 10/2015 | Reinold et al. | |

FOREIGN PATENT DOCUMENTS

| | | |
|---|---|---|
| DE | 372716 A | 3/1923 |
| DE | 1181690 B | 11/1964 |
| EP | 0543937 B1 | 1/1969 |
| JP | 2008094769 A2 | 4/2008 |

OTHER PUBLICATIONS

Kitis, M., Disinfection of wastewater with peracetic acid: a review, Environment International 30 (2004) pp. 47-55.
Ogata Y., Decomposition of peracetic acid in a mixture of acetic anhydride, acetic and nitric acids, Tetrahedron, vol. 24, Issue 21, 1968, pp. 6387-6393.

* cited by examiner

*Primary Examiner* — Paul A Zucker

(57) ABSTRACT

A method for the production of a solution of peracetic acid (PAA) containing at most 23 wt % PAA according to which acetic anhydride optionally containing acetic acid (AA) is added in a controlled manner to a diluted solution of hydrogen peroxide, wherein the diluted solution of hydrogen peroxide ($H_2O_2$) has a concentration and is used in an amount such that it if the amount of water required to hydrate all of the added acetic anhydride is subtracted therefrom, it still contains in weight, at least 50% (preferably 54%) of water based on the total amount of water and hydrogen peroxide.

13 Claims, 3 Drawing Sheets

PRODUCTION OF DISINFECTING SOLUTIONS

This invention relates to the production of disinfecting solutions, more particularly to the production of aqueous solutions of peracetic acid (PAA) and to their use as disinfecting solutions, more particularly to their production on the site of use for instance for treating flood waters (storm sewage).

Lower aliphatic peracids such as PAA are effective wide-spectrum bactericides which have the particular advantage, in use, of leaving as residues only the corresponding lower aliphatic acids (AA or acetic acid) and therefore being particularly suitable for applications which require a non-environmentally-polluting disinfectant.

An area of particular interest for the use of diluted PAA solutions is waste water treatment. When such a treatment is associated to a large industrial activity and is performed on a regular basis by specialized people, commercial PAA solutions may be shipped, stored and handled safely and quite economically. However, for medium to small entities which do not consider themselves as chemists, this storage and handling may already be too challenging (especially if large quantities are required). Such entities might prefer generating the PAA solutions only when needed and then, quickly. And in that regard, an automated process could be envisioned even for "non chemists".

Besides, for some "spot" applications especially in areas remote from industrial activity and/or PAA production, there is a need to generate on site, on the place of use, and quickly, the required PAA solutions. For instance, with the recent climate changes, floods occur more and more often which require handling quite quickly a large amount of water overflow (storm sewage) hence with a huge amount of diluted PAA which is then generated on purpose preferably on site.

Aqueous solutions of peracetic acid, including diluted ones, may be produced by reacting appropriately concentrated hydrogen peroxide and acetic acid in an aqueous medium, generally in the presence of an acid catalyst which is usually sulphuric acid or another strong mineral acid; or an organic acid like a phosphonic acid.

Such processes are for instance described in U.S. Pat. Nos. 5,349,083 and 5,368,867 in the name of the applicant. However, the time required for reaching equilibrium and/or acceptable peroxide conversion still is in the order of the days.

Besides, high amounts of sulphuric acid are used, which require a separate handling and storage and of course result in sulphate release in the environment, which is of course undesirable.

US 2015/0291520 to EVONIK industries discloses a quicker method which involves the use of methanesulfonic acid as catalyst. However, reaching 88% of conversion still takes about a day unless rather high concentrations of methanesulfonic acid are used which again have to be handled and stored separately.

U.S. Pat. No. 5,977,403 to FMC discloses an even quicker method which involves the use of acetic anhydride and a hydrogen peroxide solution having a concentration of 50 to 90 wt %. However, the method disclosed therein has several drawbacks. First, the method still requires the recourse to an acid catalyst. Second, it does not take into account the potential safety hazards (detonation problems and evacuation of heat of reaction) that may be encountered with such a process.

It is for instance known from the ternary diagram AA-H2O2-water that when adding AA to hydrogen peroxide solutions having a concentration of 50% wt or more, one ends up quite quickly in the detonation zone (see for instance U.S. Pat. Nos. 3,360,531 and 8,828.910). Besides, another known problem that can be encountered when using acetic anhydride (AAnh) instead of AA is the formation of diacyl (also called diacetyl) peroxides which are hazardous (instable) on their own and which are generated by the reaction of the anhydride with PAA. To avoid that problem, enough water should be present so that all the anhydride is hydrolyzed into AA. In its examples, the FMC patent does not provide any data on the presence/concentration of diacetyl peroxide but merely assumes there is none while in fact, there should be some according to the above considerations.

And finally, the FMC patent does not address at all the problem of handling the heat of reaction, merely reporting it in its examples without proposing a viable solution for a safe process on a large scale.

The present invention aims at solving these problems by providing a safe method for producing quickly a PAA solution, even without the use of a catalyst and nevertheless with a concentration sufficiently high to be handled and dosed (diluted) easily in a large amount of water.

To this end, the present invention concerns a method for the production of a solution of peracetic acid containing at most 23wt % PAA according to which acetic anhydride optionally containing acetic acid is added in a controlled manner to a diluted solution of hydrogen peroxide, wherein the diluted solution of hydrogen peroxide has a concentration and is used in an amount such that it if the amount of water required to hydrate all of the added acetic anhydride is subtracted therefrom, it still contains in weight, at least 50% (preferably 54%) of water based on the total amount of water and hydrogen peroxide. In other words: the diluted hydrogen peroxide solution to which the anhydride is added contains an amount of water at least equal to 50% (preferably 54%) based on the total amount of water and hydrogen peroxide, plus the amount of water required to hydrate all of the added acetic anhydride.

Figure 1:
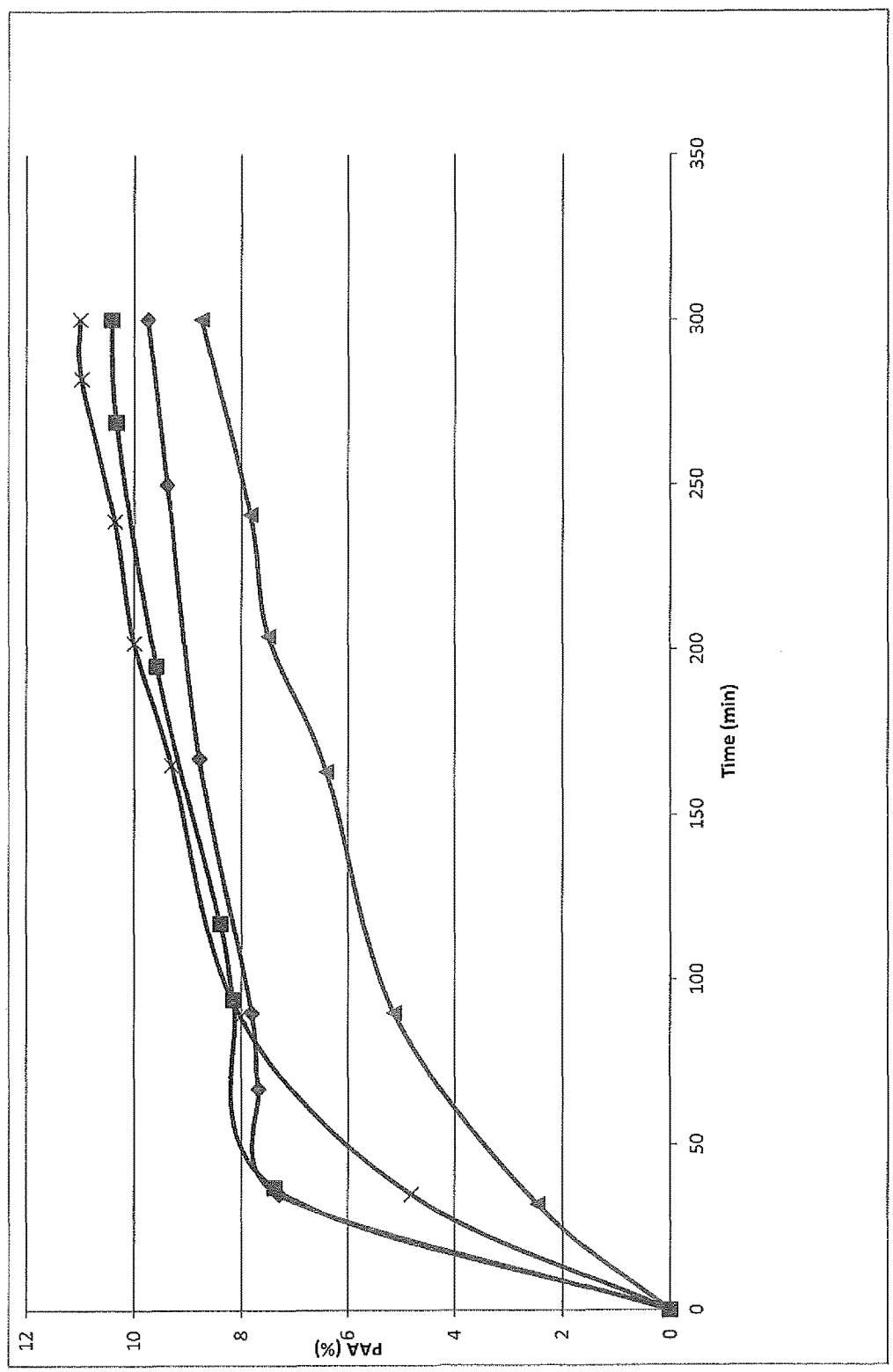
FIG. 1 shows the results of Examples 1 and 2 and Comparative Examples 7 and 8 as the percent concentration of peracetic acid ("PAA (%)") versus time, in minutes ("Time (min)").

The method of the invention can also be put into equations. It is namely so that if X=amount of water (in weight, g or kg for instance) introduced in the process through the initial hydrogen peroxide solution and optionally through additional water; Y=amount of hydrogen peroxide added through the initial hydrogen peroxide solution; and Z=amount of water (in weight, g or kg) required to hydrolyze all the anhydride added over the entire process (one mole of water being required to hydrolyze each mole of anhydride); then according to the invention, $X-Z/(X-Z+Y) \geq 0.50$, preferably $\geq 0.54$.

If water is only introduced through the initial hydrogen peroxide solution, then X=WC. Q where WC=Water Concentration (ratio, non-dimensional) of said solution and Q=quantity of said solution used (in weight); and Y=(1−WC).Q so that according to the invention:

$X-Z/(X-Z+Y)=(WC.Q-Z)/(WC.Q-Z+(1-WC).Q)$
$>=0.54$ or $(WC.Q-Z)/(Q-Z)>=0.50$, preferably $>=0.54$.

which is quite logical since it is equal to assuming that at once, all the water required to hydrolyze the anhydride from the starting solution would have been removed (taken) so that the new water concentration would indeed be calculated as being (WC.Q−Z)/(Q−Z).

This method is safe, avoiding both:
the detonation zone in the ternary AA/water/hydrogen peroxide diagram since it ensures starting from a hydrogen peroxide solution containing at least 50% (in weight) and preferably at least 54% of water; and
the formation of diacetyl peroxide because the anhydride is added gradually and in a controlled manner (namely under adequate agitation: see below) in a medium containing enough water so as to ensure that all the anhydride is hydrolyzed and prevented from reacting with PAA.

And the method of the invention can also be quick if the heat of hydration of the anhydride is allowed to heat up the reaction medium and to boost the kinetics of the reaction without requiring an external heat source. And quite surprisingly, contrary to what is taught in prior art, the method of the invention does not require the use of a catalyst either.

The peracetic acid (PAA) solution obtainable by the method of the invention comprises at most 23% PAA, preferably at most 22% PAA, more preferably at most 20% and even more preferably at most 15% of PAA. For the above mentioned application of flood water treatment, a PAA concentration of at most 10% is convenient since it offers a good compromise between its efficiency on one side (especially for flush treatment) and the speed of reaching it and the amounts of chemicals needed on the other hand.

The PAA solution obtainable by the method of the invention generally comprises at most 15% hydrogen peroxide (H2O2), knowing that it depends of course on the composition and amount of the starting media. For the above mentioned application of flood water treatment, an H2O2 concentration of about 15% is convenient and as above, constitutes a good compromise between efficiency and speed/ease of obtention.

The concentrations of water and of acetic acid (AA) of the solution of the invention are those in equilibrium with the above stated PAA and H2O2 concentrations.

In the present application, all the % are weight % versus the total weight of the concerned solutions.

The method of the invention uses acetic anhydride optionally containing AA, but preferably in a minor amount i.e. less than 50% so that there is at least 50% of the anhydride, more preferably at least 60%, and even more preferably at least 70% of the anhydride. Pure anhydride allows reaching more quickly the required concentration but since it is a chemical used in clandestine drug chemistry, it might be preferable to use anhydride diluted with at least some AA since both chemicals (the anhydride and the H2O2) have to be stored prior to their mixing according to the method of the invention. Also, an interest of diluting the anhydride lies in limiting the temperature increase effect and safety hazards associated therewith.

According to the invention, the acetic anhydride (optionally containing acetic acid) is added in a controlled manner to a diluted solution of hydrogen peroxide (which could also optionally contain a catalyst ie sulfuric acid if required, simplifying further the process). By "controlled manner" is meant added at a speed and under an agitation such that all the anhydride is effectively mixed with the diluted solution and hydrated in AA without creating locally a concentration and/or temperature that could create safety hazards. It is preferably added "dropwise" and under adequate agitation which means in fact in a way such that it can quickly be mixed with the diluted H2O2 solution. In practice, a stream of PAA solution can be injected in a controlled manner into a flow of water (through what is called a "flush treatment") which will allow both the mixing and cooling effects required.

The invention can be worked out as follows:
First, target PAA and H2O2 concentrations should be chosen and the corresponding H2O2, AA and water concentration of the starting reaction mixture should be calculated. This can be done using the equilibrium constant of the reaction (between AA and H2O2 to generate PAA and water) and conventional equilibrium concentration calculations, for instance using ICE (Initial, Change, Equilibrium) tables.

Values for the above captioned equilibrium constant are available in literature; although they may vary from one reference to another and with some parameters (including temperature and concentration(s)), assuming an average value of about 2.5 at room temperature allows calculating quite easily approximate starting compositions which may be fine-tuned using only a few experiments.

As to the above mentioned ICE tables, they lead in fine to the resolution of a quadratic equation ($ax^2+bx+c=0$) wherein the value to be determined (x) is the amount of reactants consumed, equivalent to the amount of reaction products formed. This equation can be solved using an appropriate software and/or numerical analysis method. It is namely so that the methods for solving this equation are generally iterative starting from a first estimation of the starting AA and H2O2 amounts, allowing a first calculation of x and of the related concentrations of PAA and H2O2 at equilibrium, which then in turn allow to refine/correct the estimation of the starting AA and H2O2 amounts, etc. until the target concentrations of PAA and H2O2 at equilibrium are met.

Second, knowing that the hydration of one mole of anhydride with one mole of water generates 2 moles of AA, the amounts of anhydride and water required to obtain a given amount of starting reaction mixture with the correct composition (i.e. including the water required for the hydration of the anhydride) can be determined.

Table 1 attached gives approximate starting values for some final PAA solutions and thus helps making first estimations and/or mixtures for making experiments, depending on the accuracy expected for the final composition.

The following comments/explanations are applicable to this Table 1:
columns 1 and 2 give the composition of the target PAA solutions
columns 3 to 5 give the corresponding starting amounts of water, AA and H2O2
column 6 gives the H2O2 concentration of the starting aqueous H2O2 solution prior to the addition of AA
column 7 gives a composition equivalent to the one of column 5 but where the moles of AA have been replaced by the amount of moles of anhydride (hence: the half) and water required to produce the same amount of moles of AA column 8 gives the values of X, Y and Z as defined above which correspond to the composition of column 7 column 9 gives the value of "I" which is intended to designate the value of the ratio X−Z/(X−Z+Y) explicated above and which according to the invention, should be of at least 0.50 preferably of at least 0.54.

As shown in this Table, the values indicated in columns 6 and 9 should be equal if the compositions calculated in column 7 are correct.

For example, with a target of 10% PAA and 15% H2O2 in the final solution, Table 1 recommends a starting solution containing about 50% water, 30% AA and 20% H2O2 (in weight, which implies using in 100 g of solution, 2.8 mole of H2O, 0.5 mole AA and 0.6 mole H2O2). But if starting from the anhydride instead of AA, one should use only 0.25 mole of it but an addition of 0.25 mole of water which makes in total: about 3 mole of water, 0.25 mole of anhydride and 0.6 mole of H2O2 (i.e. about 54 g of water, 26 g of anhydride and 20 g of H2O2 for 100 g of starting solution, or 540 kg/260 kg/200 kg respectively for each of these ingredients for 1 ton of solution).

Similar calculations can of course be made if not all the AA is replaced with the anhydride and again, the results can be fine-tuned with a limited number of experiments.

Since 100% H2O2 solutions are not commercially available, all the above calculations should be adapted to take into account the strength of the H2O2 solution actually used.

As explained above, the present invention preferably uses the heat of hydration of the anhydride in order to boost the reaction kinetics. Hence, in the present invention, the anhydride hydration and the subsequent reaction between AA and H2O2 are preferably carried out without cooling the reaction medium i.e. by letting the temperature evolve naturally—but preferably under control though, avoiding local hot spots.

As explained above, the process of the invention is advantageously used to produce a PAA solution on the site where it is used for instance in water treatment, pulp & paper, food industry, laundry animal farming or aquaculture.

In a preferred embodiment, the process of the invention is used to treat on site, waste water and more preferably, sewage water especially arising after a storm.

According to that embodiment, a "concentrated" PAA solution (comprising preferably a few % of PAA though) is first synthesized as explained above and it is then further diluted/injected in the water to be treated so as to reach a desired PAA concentration. In water treatment, this concentration is generally in the range of the ppm (from 5 to 20 ppm for instance). In practice, for sewage water, this can for instance be done by injecting one or several jets of the concentrated solution in the water flow.

In another preferred embodiment, the process of the invention is used on site of a pulp & paper plant, for instance in a straw bleaching facility which makes paper out of straw.

In the embodiments where the solution is produced on its site of use, one important parameter is the speed at which the PAA solution can be made available in order to be able to treat storm water as soon as possible after the storm has begun. Therefore, in a preferred embodiment, the concentrated solution is used before equilibrium is reached, for instance when only 80% conversion is reached. This is made possible thanks to the kinetics of reaction when using the anhydride instead of AA, which generally allows reaching 80% of conversion over maximum 5 hours, even after 3 hours and even, after 1 hour already in some embodiments as will be shown through the Examples below. It is namely so that the heat of hydration of the anhydride favours the reaction at its very beginning which is very useful for this kind of application where a high concentration of PAA should be available quite quickly without wasting too much chemicals.

EXAMPLE 1

In a 500 ml glass container, a 50% H2O2 solution and DMW (demineralized water) were introduced. The liquid was agitated using a magnetic stirrer (at a speed of 400 rpm) and acetic anhydride (AnHAc) was added dropwise at a speed of 1 ml/min.

The concentration of PAA generated was measured over time using the well-known method of iodometric titration. There was an increase of temperature up to 47,2° C. in the first 10 min.

The amounts of reactives used (which correspond to the above mentioned target of 10% PAA and 15% H2O2 in the final solution, as can be seen from the molar concentration of the reactives used, calculated with respect to "pure" chemicals, which means that the 50% H2O2 solution has been converted to the corresponding moles of H2O2 and water, the latter being added to the moles of DMW) and the results obtained are shown in Table 2 below.

EXAMPLE 2

The procedure of Example 1 was repeated but using additionally 3% H2SO4 as indicated in Table 2 below, which also shows the results obtained.

There was an increase of temperature up to 60° C. in the first 10 min.

EXAMPLES 3 to 6

The procedure of Example 1 was repeated but using AnHAc mixed with AA in the amounts indicated in Table 2 below, which also show the results obtained and the values of X, Y, Z and I as defined above.

COMPARATIVE EXAMPLES 7 to 10

The procedure of Example 1 set forth above was repeated but using AA and a catalyst, the nature (sulphuric acid or methanesulfonic acid, added as last component at a speed of 0.05 ml (or 1 drop) per second) and amount of which is indicated in Table 3 below, which also show the results obtained.

Figure 2:
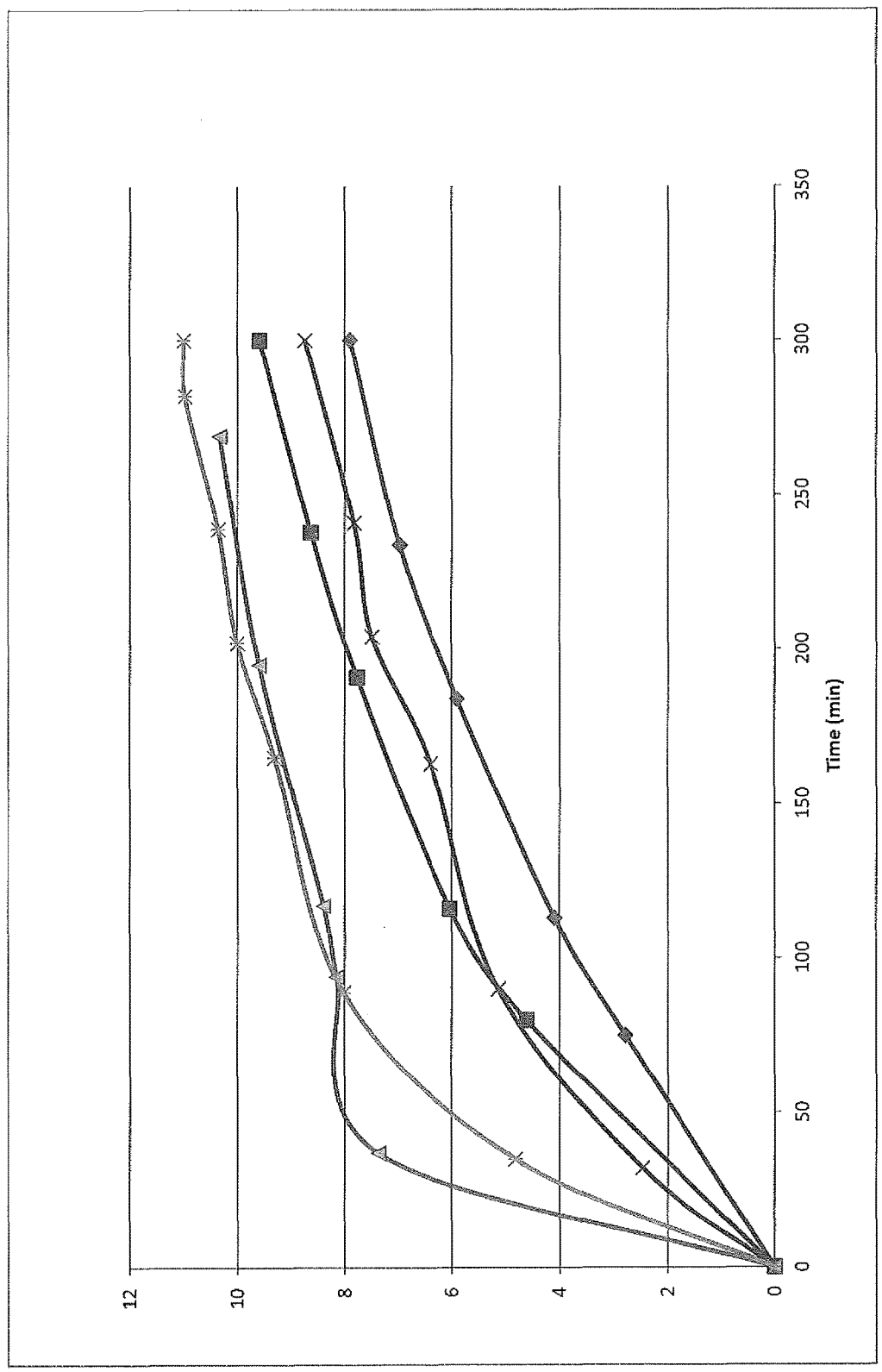
FIG. 2 shows the results of Example 1 and Comparative Examples 7, 8, 9, and 10, as the percent concentration of peracetic acid ("PAA (%)") versus time, in minutes ("Time (min)").
Figure 3:
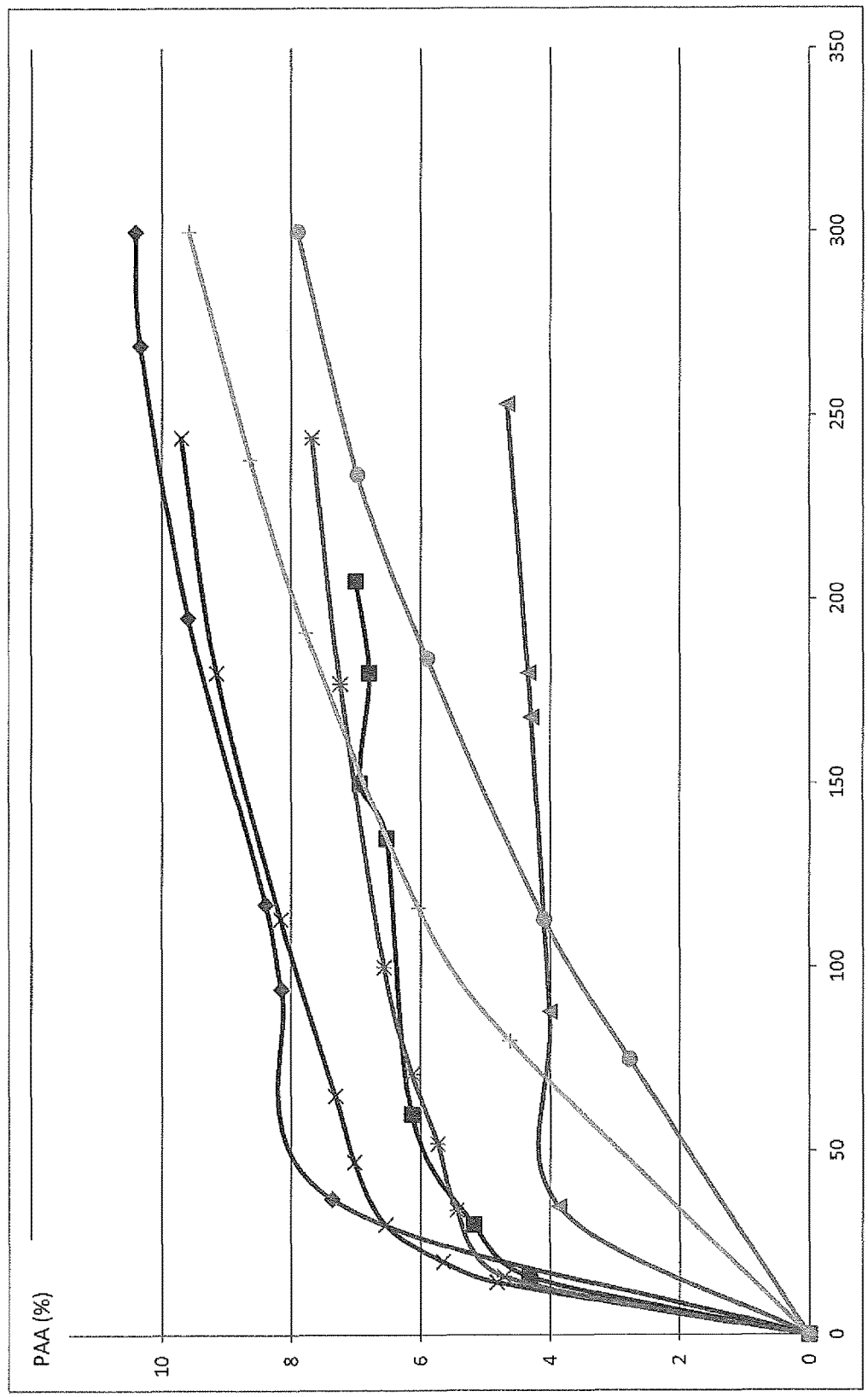
FIG. 3 shows the results of Examples 1, 3, 4, 5, and 6 and Comparative Examples 9 and 10, as the percent concentration of peracetic acid ("PAA (%)") versus time, in minutes ("Time (min)").

The results obtained in the Examples and Comparative Examples set forth above are illustrated and compared in FIGS. 1-3 attached.

FIG. 1 shows the results of Examples 1 (squares) and 2 (diamonds) and Comparative Examples 7 (triangles) and 8 (angled crosses).

FIG. 2 shows the results of Example 1 (triangles) and Comparative Examples 7 (angled crosses), 8 (asterisks), 9 (diamonds) and 10 (squares).

FIG. 3 shows the results of Examples 1 (diamonds), 3 (angled crosses), 4 (asterisks), 5 (squares) and 6 (triangles) and Comparative Examples 9 (circles) and 10 (vertical crosses).

The invention claimed is:

1. A method for making a solution of peracetic acid, containing at most 23 wt % peracetic acid, for use in an intended end use application at an end use site, comprising adding acetic anhydride, optionally containing acetic acid, in a controlled manner to a dilute solution of hydrogen peroxide, wherein the amount and concentration of the dilute solution of hydrogen peroxide are such that: if the amount of water required to hydrate all of the added acetic anhydride were to be subtracted therefrom, then the resulting dilute solution would contain at least 50 wt % of water, based on the total amount of water and hydrogen peroxide, wherein the peracetic acid solution is made at the end use site and is used before the equilibrium concentration of peracetic acid for the peracetic acid solution is reached.

2. The method according to claim 1, wherein the solution of peracetic acid comprises at most 15 wt % hydrogen peroxide.

3. The method according to claim 1, wherein the acetic anhydride is pure acetic anhydride.

4. The method according to claim 1, wherein the acetic anhydride comprises a minor amount of acetic acid.

5. The method according to claim 1, wherein method is carried out without actively cooling the combined dilute solution and added acetic anhydride.

6. The method according to claim 1, wherein the intended end use application is an application in water treatment, pulp and paper, food industry, laundry, animal farming, or aquaculture.

7. The method according to claim 6, wherein the intended end use application is to treat waste water.

8. The method according to claim 6, wherein the peracetic acid solution contains about 10 wt % peracetic acid.

9. The method according to claim 6, wherein the peracetic acid solution contains about 15 wt % hydrogen peroxide.

10. The method according to claim 6, wherein the peracetic acid solution is made and used on site of a pulp and paper plant.

11. The method of claim 1, wherein the amount and concentration of the dilute solution of hydrogen peroxide are such that: if the amount of water required to hydrate all of the added acetic anhydride is subtracted therefrom, then the resulting dilute hydrogen peroxide solution would contain at least 54 wt % of water, based on the total amount of water and hydrogen peroxide.

12. The method according to claim 7, wherein the waste water comprises sewage water and the intended end use application is to treat the waste water after a storm.

13. The method according to claim 1, wherein the peracetic acid solution is used at a time that is after 80% conversion of acetic anhydride to peracetic acid and before the equilibrium concentration of peracetic acid for the peracetic acid solution is reached.

* * * * *